US00PP29505P2

(12) United States Plant Patent
Xinkai et al.

(10) Patent No.: US PP29,505 P2
(45) Date of Patent: Jul. 17, 2018

(54) ***CAMELLIA* PLANT NAMED 'HA011'**

(50) Latin Name: ***Camellia changii* X *Camellia japonica***
Varietal Denomination: HA011

(71) Applicants: Liu Xinkai, Guangzhou (CN); Huang Wanjian, Guangzhou (CN); Xu Hui, Guangzhou (CN)

(72) Inventors: Liu Xinkai, Guangzhou (CN); Huang Wanjian, Guangzhou (CN); Xu Hui, Guangzhou (CN)

(73) Assignee: Palm Eco-Town Development Co. Ltd., Guangzhou (CN)

( * ) Notice: Subject to any disclaimer, the term of this patent is extended or adjusted under 35 U.S.C. 154(b) by 36 days.

(21) Appl. No.: 15/530,356

(22) Filed: Dec. 30, 2016

(51) Int. Cl.
*A01H 5/00* (2018.01)

(52) U.S. Cl.
USPC ..... Plt./243

(58) Field of Classification Search
USPC ..... Plt./226, 243
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Camellia* plant named 'HA011', characterized by its sturdy upright plant habit; rapid growth habit; freely branching habit; dense and bushy appearance; leathery dark green-colored leaves; flowering during the summer, autumn and winter; large red and light pink-colored semi-double flowers; and good garden performance.

2 Drawing Sheets

Botanical designation: *Camellia changii* X *Camellia japonica.*
Cultivar denomination: 'HA011'.

CROSS-REFERENCED TO CLOSELY RELATED APPLICATIONS

Title: *Camellia* Plant Named 'HA012'
Applicants: Gao Jiyin, Li Yanling & Ye Qijun
Filed: Concurrently with this application

BACKGROUND OF THE INVENTION

The present Invention relates to a new and distinct cultivar of *Camellia* plant, botanically known as *Camellia changii* X *Camellia japonica*, and hereinafter referred to by the name 'HA011'.

The new *Camellia* plant is a product of a planned breeding program conducted by the Inventors in Zhaoqing, China. The objective of the breeding program is to create new fast-growing *Camellia* plants that flower year-round and tolerate full sunlight.

The new *Camellia* plant originated from a cross-pollination conducted by the Inventors in October, 2006 in Zhaoqing, China of an unnamed seedling selection of *Camellia changii*, not patented, as the female, or seed, parent with *Camellia japonica* 'Kramer's Supreme', not patented, as the male, or pollen, parent. The new *Camellia* plant was discovered and selected by the Inventors as a single plant from within the progeny of the stated cross-pollination in a controlled environment in Zhaoqing, China in September, 2011.

Asexual reproduction of the new *Camellia* plant by grafting cuttings onto an unnamed selection of *Camellia gaozhouensis*, not patented, in a controlled greenhouse environment in Zhaoqing, China has shown that the unique features of this new *Camellia* plant are stable and reproduced true to type in successive generations.

SUMMARY OF THE INVENTION

Plants of the new *Camellia* have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'HA011'. These characteristics in combination distinguish 'HA011' as a new and distinct cultivar of *Camellia:*

1. Sturdy upright plant habit.
2. Rapid growth habit.
3. Freely branching habit, dense and bushy appearance.
4. Leathery dark green-colored leaves.
5. Flowering during the summer, autumn and winter.
6. Large red and light pink-colored semi-double flowers.
7. Good garden performance, tolerant to full sunlight conditions.

Plants of the new *Camellia* differ from plants of the female parent selection primarily in the following characteristics:

1. Leaves of plants of the new *Camellia* are obovate in shape whereas leaves of plants of the female parent selection are lanceolate in shape.
2. Leaves of plants of the new *Camellia* have serrate margins whereas leaves of plants of the female parent selection have entire margins.
3. Flowers of plants of the new *Camellia* are semi-double in form whereas flowers of the female parent selection are single in form.

Plants of the new *Camellia* differ primarily from plants of the male parent, 'Kramer's Supreme', in the following characteristics:

1. Margins of leaves of plants of the new *Camellia* are not as serrate as margins of leaves of plants of 'Kramer's Supreme'.
2. Plants of the new *Camellia* and 'Kramer's Supreme' differ in flower color as plants of 'Kramer's Supreme' have solid red-colored flowers.
3. Plants of the new *Camellia* flower multiple times during the year whereas plants of plants of 'Kramer's Supreme' flower once a year.

Plants of the new *Camellia* can be compared to plants of *Camellia changii* X *Camellia japonica* 'HA012', disclosed in a U.S. Plant patent application Ser. No. 15/530,358 filed concurrently. Plants of the new *Camellia* and 'HA012' differ primarily in flower color as plants of 'HA012' have solid light red-colored flowers.

Plants of the new *Camellia* can also be compared to the plants of *Camellia* 'Hua Mu Dan', not patented. In side-by-side comparisons plants of the new *Camellia* differ from plants of the 'Hua Mu Dan' in the following characteristics:

1. Flowers of plants of the new *Camellia* are faintly fragrant whereas flowers of plants of 'Hua Mu Dan' are not fragrant.
2. Plants of the new *Camellia* flower multiple times during the year whereas plants of plants of 'Hua Mu Dan' only flower one time each year.

BRIEF DESCRIPTION OF THE PHOTOGRAPHS

The accompanying colored photographs illustrate the overall appearance of the new *Camellia* plant showing the colors as true as it is reasonably possible to obtain in colored reproductions of this type. Colors in the photographs may differ slightly from the color values cited in the detailed botanical description, which accurately describe the colors of the new *Camellia* plant.

The photograph on the first sheet is a side perspective view of a typical flowering plant of 'HA011' grown in a container.

The photograph on the second sheet are close-up view of typical vegetive stems, developing flower buds and developing flowers of 'HA011'.

DETAILED BOTANICAL DESCRIPTION

The aforementioned photographs and following observations and measurements describe plants grown in Zhaoqing, China in an outdoor nursery during the late autumn and under cultural practices typical of commercial *Camellia* production. During the production of the plants, day temperatures averaged 22° C. and night temperatures averaged 18° C. Plants were five years old when the photographs and description were taken. In the following description, color references are made to The Royal Horticultural Society Colour Chart, 2001 Edition, except where general terms of ordinary dictionary significance are used.

Botanical classification: *Camellia changii* X *Camellia japonica* 'HA011'.

Parentage:

*Female, or seed, parent*.—Unnamed seedling selection of *Camellia changii*, not patented.

*Male, or pollen, parent*.—*Camellia japonica* 'Kramer's Supreme', not patented.

Propagation:

*Type*.—By grafting cuttings onto a rootstock, an unnamed selection of *Camellia gaozhouensis*, not patented.

*Time to produce a rooted young plant, summer*.—About two months days at temperatures about 28° C.

*Time to produce a rooted young plant, winter*.—About two months days at temperatures about 8° C.

Plant description:

*Plant form and growth habit*.—Perennial evergreen shrub; sturdy upright plant habit; vigorous growth habit; rapid growth rate.

*Branching habit*.—Freely branching habit; about two to three primary lateral branches each with about two to three secondary branches; dense and bushy appearance.

*Plant height*.—About 198 cm.

*Plant diameter, area of spread*.—About 130 cm.

*Lateral branch description*.—Length, secondary branches: About 45 cm. Diameter: About 4 mm. Internode length: About 2.1 cm. Strength: Strong. Aspect: Upright to about 20° to 30° from vertical. Texture and luster: Smooth, glabrous; matte; woody with development. Color, young stems: Close to 199A; at the internodes, close to 193B. Color, older stems: Close to 199B.

*Leaf description*.—Arrangement: Alternate, single. Length: About 9.2 cm. Width: About 4.1 cm. Shape: Obovate. Apex: Acuminate. Base: Cuneate. Margin: Serrate. Venation pattern: Pinnate, arcuate. Texture and luster, upper surface: Smooth, glabrous; leathery; moderately glossy. Texture and luster, lower surface: Smooth, glabrous; leathery; matte. Color: Developing leaves, upper surface: Close to 146A. Developing leaves, lower surface: Close to 147B. Fully expanded leaves, upper surface: Close to N137A; venation, close to 137B; color does not change with the seasons. Fully expanded leaves, lower surface: Close to 137B; venation, close to 144A; color does not change with the seasons.

*Petioles*.—Length: About 1.2 cm. Diameter: About 2 mm. Texture and luster, upper and lower surfaces: Smooth, glabrous; moderately glossy. Color, upper and lower surfaces: Close to 137A.

Flower description:

*Flower arrangement and appearance*.—Semi-double rotate flowers, flowers terminal and axillary; freely flowering habit with usually about 28 flowers and flower buds developing per plant; flowers face mostly upright to outwardly.

*Natural flowering season*.—Plants of the new *Camellia* flower during the summer, autumn and winter in Zhaoqing, China.

*Postproduction longevity*.—Plants maintain good flower substance for about eight days on the plant; flowers persistent.

*Fragrance*.—Faintly fragrant.

*Flower diameter*.—Large, about 11.8 cm.

*Flower depth*.—About 6.5 cm.

*Flower buds*.—Length: About 3.2 cm. Diameter: About 2.5 cm. Shape: Ovoid. Texture and luster: Smooth, glabrous; matte. Color: Close to 46A.

*Petals*.—Quantity and arrangement: About 19 imbricate petals arranged in numerous whorls. Length: About 5.5 cm. Width: About 4.1 cm. Shape: Broadly obovate. Apex: Obcordate. Base: Cuneate. Margin:

Entire; slightly undulate. Texture and luster, upper and lower surfaces: Smooth, glabrous; matte. Color: When opening, upper and lower surfaces: Random sectors, close to 52A and N155B. Fully opened, upper and lower surfaces: Random sectors, close to 65C and 54A; venation, close to 65B and 54A; color does not change with development.

*Petaloids*.—Quantity and arrangement: About six petaloids at the center of the flower. Length: About 6 cm. Width: About 3 cm. Shape: Obovate. Apex: Obcordate. Base: Cuneate. Margin: Entire; moderately undulate. Texture and luster, upper and lower surfaces: Smooth, glabrous; matte. Color: When opening, upper surface: Close to 53C. When opening, lower surface: Close to 47A. Fully opened, upper surface: Close to 53C; venation, close to 53C; color does not change with development. Fully opened, lower surface: Close to 47A; venation, close to 47A; color does not change with development.

*Sepals*.—Quantity and arrangement: About seven to eight imbricate sepals arranged in a shallow cup-shaped calyx. Length: About 1.6 cm. Width: About 1.2 cm. Shape: Broadly elliptical. Apex: Obtuse. Base: Rotund. Margin: Entire. Texture and luster, upper and lower surfaces: Smooth, glabrous; leathery; moderately glossy. Color: When opening, upper surface: Close to 145B. When opening, lower surface: Close to 146D. Fully opened, upper surface: Close to 147C. Fully opened, lower surface: Close to 148A.

*Peduncles*.—Length: About 3 mm. Diameter: About 4 mm. Aspect: About 25° to 35° from stem axis. Strength: Strong. Texture and luster: Smooth, glabrous; matte. Color: Close to 146B.

*Reproductive organs*.—Androecium: Quantity per flower: About 284. Filament length: About 3.2 cm. Filament color: Close to 29B. Anther shape: Oblong. Anther size: About 1.5 mm by 1 mm. Anther color: Close to 17A. Pollen amount: Scarce. Pollen color: Close to 17A. Gynoecium: Quantity of pistils per flower: Four-parted. Pistil length: About 2.3 cm. Style length: About 2.2 cm. Style color: Close to 29D. Stigma color: Close to 29D. Ovary color: Close to 6C.

*Fruits and seeds*.—Fruit and seed production have not been observed on plants of the new *Camellia*.

Garden performance: Plants of the new *Camellia* have been observed have good garden performance and to tolerate rain, wind, full sunlight and temperatures ranging from about −10° C. to about 40° C.

Disease & pest resistant: Plants of the new *Camellia* have not been observed to be resistant to pathogens and pests common to *Camellia* plants.

It is claimed:

1. A new and distinct cultivar of *Camellia* plant named 'HA011' as illustrated and described.

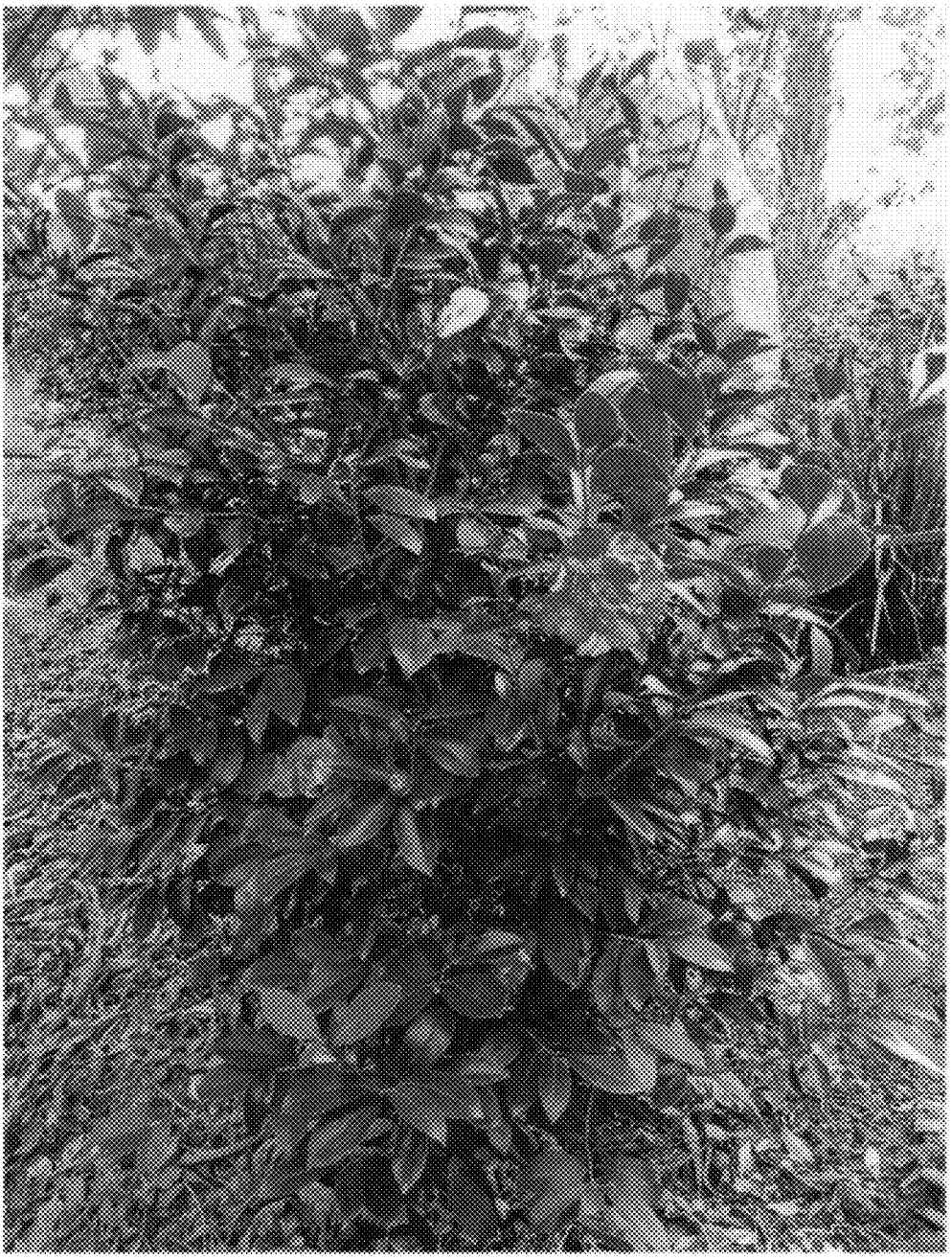

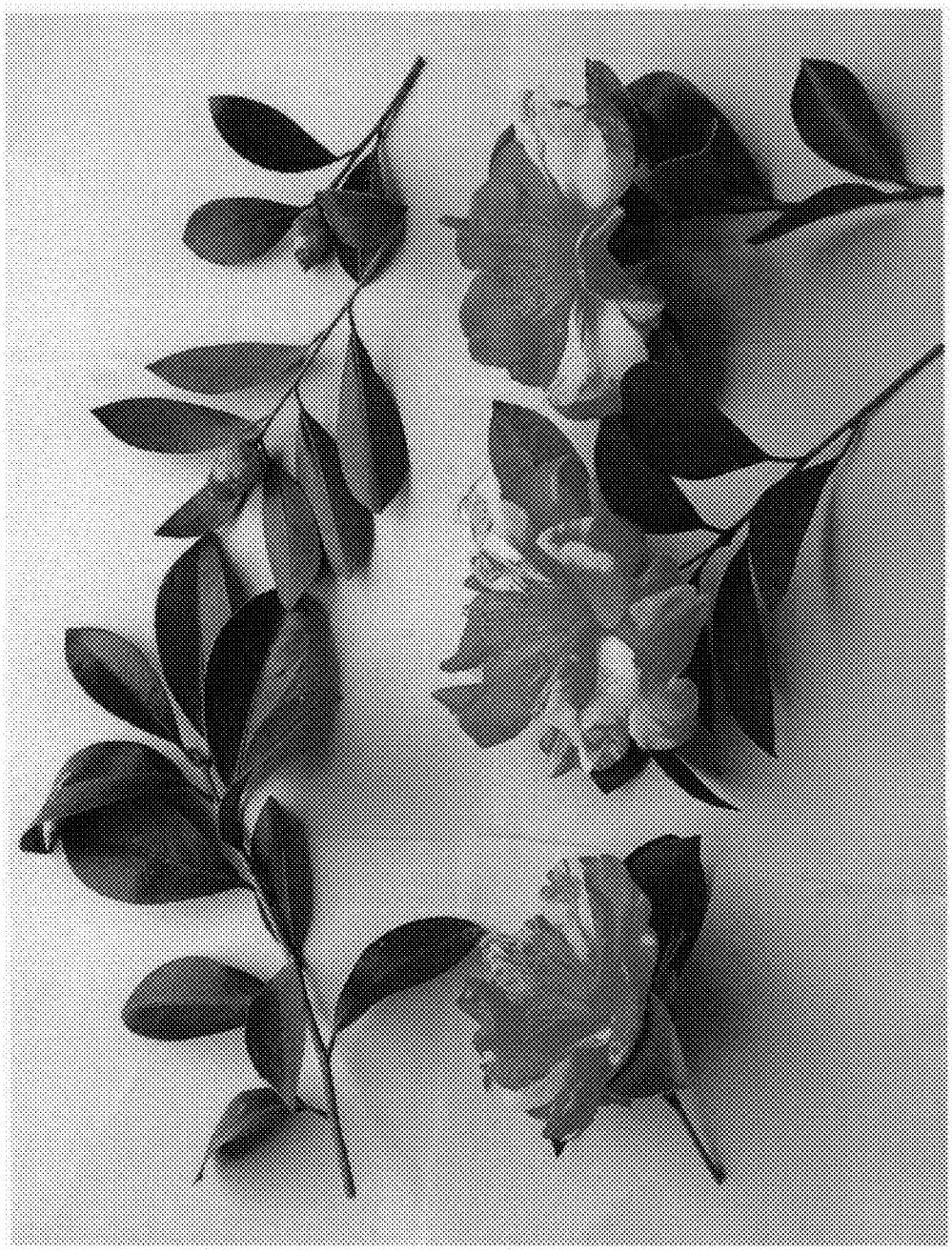

* * * * *